United States Patent [19]

Morozowich

[11] 4,205,011
[45] May 27, 1980

[54] INTER-PHENYLENE-ω-ARYL-PG AMIDES

[75] Inventor: Walter Morozowich, Kalamazoo Township, Kalamazoo County, Mich.

[73] Assignee: The Upjohn Company, Kalamazoo, Mich.

[21] Appl. No.: 898,224

[22] Filed: Apr. 20, 1978

Related U.S. Application Data

[63] Continuation-in-part of Ser. No. 788,455, Apr. 18, 1977, Pat. No. 4,100,192.

[51] Int. Cl.$^2$ ............................................. C07C 103/20
[52] U.S. Cl. .............................. 260/558 R; 260/558 P; 260/559 D; 260/559 P; 260/559 B; 260/559 R
[58] Field of Search ............ 260/558 R, 558 P, 559 D, 260/559 P, 559 B, 559 R

[56] References Cited

U.S. PATENT DOCUMENTS

| | | | |
|---|---|---|---|
| 3,933,895 | 1/1976 | Nelson | 260/473 A |
| 3,933,897 | 1/1976 | Nelson | 260/473 A |
| 3,933,898 | 1/1976 | Nelson | 260/473 A |
| 3,933,899 | 1/1976 | Nelson | 260/473 A |
| 3,933,900 | 1/1976 | Nelson | 260/473 A |
| 4,044,043 | 4/1977 | Bernady et al. | 260/468 D |

*Primary Examiner*—Arthur P. Demers
*Attorney, Agent, or Firm*—Robert A. Armitage

[57] ABSTRACT

The present invention relates to inter-phenylene-ω-aryl-PG amides. These compounds are pharmacological agents, being prolonged orally active platelet aggregation inhibitors in mammalian species. These compounds are accordingly useful for antithrombotic applications.

48 Claims, No Drawings

INTER-PHENYLENE-ω-ARYL-PG AMIDES

CROSS REFERENCE TO RELATED APPLICATIONS

This application is a continuation-in-part of Ser. No. 788,455, filed Apr. 18, 1977, now U.S. Pat. No. 4,100,192, issued July 11, 1978.

The present invention relates to inter-phenylene-ω-aryl-PG amides, the essential material constituting a disclosure of which is incorporated here by reference from Ser. No. 788,455. In particular, the present invention relates to inter-phenylene-ω-aryl-PG amides of the unsubstituted inter-phenylene PG amides described in Ser. No. 788,455 now U.S. Pat. No. 4,100,192.

The present invention is particularly concerned with the following compounds:

3,7-Inter-m-phenylene-3-oxa-16-phenoxy-4,5,6,17,18,19,20-heptanor-11-deoxy-PGF$_{1\alpha}$, amide;
3,7-Inter-m-phenylene-3-oxa-16-phenoxy-4,5,6,17,18,19,20-heptanor-PGF$_{1\alpha}$, amide;
3,7-Inter-m-phenylene-3-oxa-16-phenoxy-4,5,6,17,18,19,20-heptanor-9-deoxy-PGD$_1$, amide;
3,7-Inter-m-phenylene-3-oxa-16-phenoxy-4,5,6,17,18,19,20-heptanor-PGD$_1$, amide;
3,7-Inter-m-phenylene-3-oxa-16-phenoxy-4,5,6,17,18,19,20-heptanor-9-deoxy-9,10-didehydro-PGD$_1$, amide;
3,7-Inter-m-phenylene-3-oxa-15-phenoxy-4,5,6,17,18,19,20-heptanor-PGA$_1$, amide;
3,7-Inter-m-phenylene-3-oxa-16-phenoxy-4,5,6,17,18,19,20-heptanor-11-deoxy-PGE$_1$, amide;
3,7-Inter-m-phenylene-3-oxa-16-phenoxy-4,5,6,17,18,19,20-heptanor-cis-13-PGE$_1$, amide;
3,7-Inter-m-phenylene-3-oxa-16-phenoxy-4,5,6,17,18,19,20-heptanor-13,14-dihydro-PGE$_1$, amide;
3,7-Inter-m-phenylene-16-phenoxy-4,5,6,17,18,19,20-heptanor-PGE$_1$, amide;
15-Epi-3,7-Inter-m-phenylene-3-oxa-16-phenoxy-4,5,6,17,18,19,20-heptanor-PGE$_1$, amide;
3,7-inter-m-phenylene-3-oxa-17-phenyl-4,5,6,17,18,19,20-heptanor-PGE$_1$, amide;
3,7-inter-m-phenylene-3-oxa-17-phenyl-4,5,6,17,18,19,20-heptanor-PGE$_1$, amide;
2a,2b-Dihomo-3,7-inter-m-phenylene-3-oxa-4,5,6,17,18,19,20-heptanor-PGE$_1$, amide;
3,7-Inter-m-phenylene-3-oxa-16-phenoxy-4,5,6,18,19,20-hexanor-16-methyl-PGE$_1$, amide;
3,7-Inter-m-phenylene-3-oxa-16-phenoxy-4,5,6,17,18,19,20-heptanor-16-methyl-PGE$_1$, amide;
3,7-Inter-m-phenylene-3-oxa-16-phenoxy-4,5,6,17,18,19,20-heptanor-PGE$_1$, n-propylamide;
3,7-Inter-m-phenylene-3-oxa-16-phenoxy-4,5,6,17,18,19,20-heptanor-PGE$_1$, ethylamide; and
3,7-Inter-m-phenylene-3-oxa-16-phenoxy-4,5,6,17,18,19,20-heptanor-PGE$_1$, methylamide.

I claim:
1. A prostaglandin analog of the formula

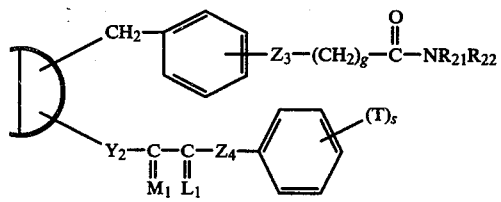

wherein D is

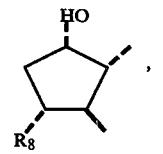

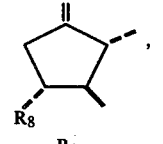

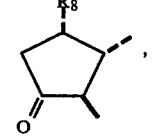

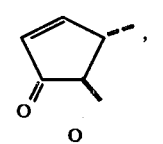

wherein $R_8$ is hydrogen or hydroxy;
wherein $Y_1$ is
 (1) trans—CH=CH—, or
 (2) cis—CH=CH—,
wherein g is one, 2, or 3;
wherein $Z_3$ is oxa or methylene;
wherein $L_1$ is

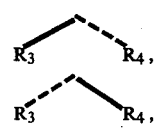

or a mixture of

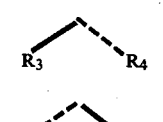

and wherein $R_3$ and $R_4$ are hydrogen, methyl, or fluoro, being the same or different, with the proviso that one of $R_3$ and $R_4$ is methyl only when the other is hydrogen or methyl;
wherein $M_1$ is

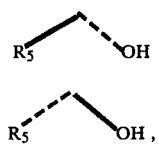
or
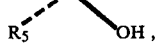

wherein R$_5$ is hydrogen or methyl;
wherein R$_{21}$ and R$_{22}$ are
(i) hydrogen;
(ii) alkyl of one to 12 carbon atoms, inclusive;
(iii) cycloalkyl of 3 to 10 carbon atoms, inclusive;
(iv) aralkyl of 7 to 12 carbon atoms, inclusive;
(v) phenyl;
(vi) phenyl substituted with one, 2, or 3 chloro, alkyl of one to 3 carbon atoms, inclusive, hydroxy or nitro;
(vii) hydroxyalkyl of one to 4 carbon atoms, inclusive;
(viii) dihydroxyalkyl of one to 4 carbon atoms; or
(ix) trihydroxyalkyl of one to 4 carbon atoms;
with the further proviso that not more than one of R$_{21}$ and R$_{22}$ is other than hydrogen or alkyl.
wherein Z$_4$ is —(CH$_2$)$_h$ or oxa, wherein h is zero to 3, inclusive, and
wherein s is zero, one, 2, or 3, and T is chloro, fluoro, trifluoromethyl, alkyl of one to 3 carbon atoms, or alkoxy of one to 3 carbon atoms, the various T's being the same or different, with the proviso that not more than two T's are other than alkyl.

2. A prostaglandin analog according to claim 1, wherein D is

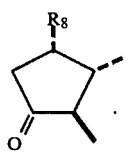

3. A prostaglandin analog according to claim 2, wherein R$_8$ is hydrogen.
4. 3,7-inter-m-Phenylene-3-oxa-16-phenoxy-4,5,6,17,18,19,20-heptanor-11-deoxy-PGF$_{1\alpha}$, amide, a prostaglandin analog according to claim 3.
5. A prostaglandin analog according to claim 2, wherein R$_8$ is hydroxy.
6. 3,7-inter-m-Phenylene-3-oxa-16-phenoxy-4,5,6,17,18,19,20-heptanor-PGF$_{1\alpha}$, amide, a prostaglandin analog according to claim 5.
7. A prostaglandin analog according to claim 1, wherein D is

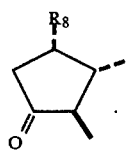

8. A prostaglandin analog according to claim 7, wherein R$_8$ is hydrogen.

9. 3,7-inter-m-Phenylene-3-oxa-16-phenoxy-4,5,6,17,18,19,20-heptanor-9-deoxy-PGD$_1$, amide, a prostaglandin analog according to claim 8.
10. A prostaglandin analog according to claim 7, wherein R$_8$ is hydroxy.
11. 3,7-inter-m-Phenylene-3-oxa-16-phenoxy-4,5,6,17,18,19,20-heptanor-PGD$_1$, amide, a prostaglandin analog according to claim 10.
12. A prostaglandin analog according to claim 1, wherein D is

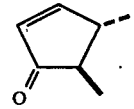

13. 3,7-inter-m-Phenylene-3-oxa-16-phenoxy-4,5,6,17,18,19,20-heptanor-9-deoxy-9,10-didehydro-PGD$_1$, amide, a prostaglandin analog according to claim 12.
14. A prostaglandin analog according to claim 1, wherein

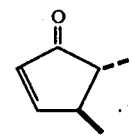

15. 3,7-inter-m-Phenylene-3-oxa-16-phenoxy-4,5,6,17,18,19,20-heptanor-PGA$_1$, amide, a prostaglandin analog according to claim 14.
16. A prostaglandin analog according to claim 1, wherein

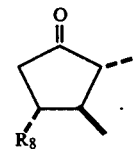

17. A prostaglandin analog according to claim 16, wherein R$_8$ is hydrogen.
18. 3,7-inter-m-Phenylene-3-oxa-16-phenoxy-4,5,6,17,18,19,20-heptanor-11-deoxy-PGE$_1$, amide, a prostaglandin analog according to claim 17.
19. A prostaglandin analog according to claim 16, wherein R$_8$ is hydroxy.
20. A prostaglandin analog according to claim 19, wherein Y$_1$ is cis—CH=CH—.
21. 3,7-inter-m-Phenylene-3-oxa-16-phenoxy-4,5,6,17,18,19,20-heptanor-cis-13-PGE$_1$, amide, a prostaglandin analog according to claim 20.
22. A prostaglandin analog according to claim 19, wherein Y$_1$ is —CH$_2$CH$_2$—.
23. 3,7-inter-m-Phenylene-3-oxa-16-phenoxy-4,5,6,17,18,19,20-heptanor-13,14-dihydro-PGE$_1$, amide, a prostaglandin analog according to claim 22.
24. A prostaglandin analog according to claim 19, wherein Y$_1$ is trans—CH=CH—.
25. A prostaglandin analog according to claim 24, wherein Z$_3$ is methylene.
26. A prostaglandin analog according to claim 25, wherein Z$_3$ is attached to the phenyl ring in the position meta to methylene.

27. 3,7-inter-m-Phenylene-16-phenoxy-4,5,6,17,18,19,20-heptanor-PGE$_1$, amide, a prostaglandin analog according to claim 26.

28. A prostaglandin analog according to claim 24, wherein Z$_3$ is oxa.

29. A prostaglandin analog according to claim 28, wherein M$_1$ is

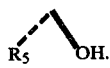

30. 15-epi-3,7-inter-m-Phenylene-3-oxa-16-phenoxy-4,5,6,17,18,19,20-heptanor-PGE$_1$, amide, a prostaglandin analog according to claim 29.

31. A prostaglandin analog according to claim 28, wherein M$_1$ is

32. A prostaglandin analog according to claim 31, wherein Z$_3$ is attached to the phenyl ring in the position meta to methylene.

33. A prostaglandin analog according to claim 32, wherein Z$_4$ is —(CH$_2$)$_h$.

34. 3,7-inter-m-Phenylene-3-oxa-17-phenyl-4,5,6,17,18,19,20-heptanor-PGE$_1$, amide, a prostaglandin analog according to claim 33.

35. A prostaglandin analog according to claim 32, wherein Z$_4$ is oxa.

36. A prostaglandin analog according to claim 32, wherein s is zero or one and T is chloro, fluoro, or trifluoromethyl.

37. A prostaglandin analog according to claim 36, wherein g is 3.

38. 2a,2b-Dihomo-3,7-inter-m-phenylene-3-oxa-4,5,6,17,18,19,20-heptanor-PGE$_1$, amide, a prostaglandin analog according to claim 37.

39. A prostaglandin analog according to claim 36, wherein g is one.

40. A prostaglandin analog according to claim 39, wherein at least one of R$_3$ and R$_4$ is methyl.

41. 3,7-inter-m-Phenylene-3-oxa-16-phenoxy-4,5,6,18,19,20-hexanor-16-methyl-PGE$_1$, amide, a prostaglandin analog according to claim 49.

42. A prostaglandin analog according to claim 39, wherein R$_3$ and R$_4$ are both hydrogen.

43. A prostaglandin analog according to claim 42, wherein R$_5$ is methyl.

44. 3,7-inter-m-Phenylene-3-oxa-16-phenoxy-4,5,6,17,18,19,20-heptanor-15-methyl-PGE$_1$, amide, a prostaglandin analog according to claim 43.

45. A prostaglandin analog according to claim 42, wherein R$_5$ is hydrogen.

46. 3,7-inter-m-Phenylene-3-oxa-16-phenoxy-4,5,6,17,18,19,20-heptanor-PGE$_1$, n-propylamide, a prostaglandin analog according to claim 45.

47. 3,7-inter-m-Phenylene-3-oxa-16-phenoxy-4,5,6,17,18,19,20-heptanor-PGE$_1$, ethylamide, a prostaglandin analog according to claim 45.

48. 3,7-inter-m-Phenylene-3-oxa-16-phenoxy-4,5,6,17,18,19,20-heptanor-PGE$_1$, methylamide, a prostaglandin analog according to claim 45.

* * * * *

UNITED STATES PATENT OFFICE
CERTIFICATE OF CORRECTION

Patent No. 4,205,011        Dated 27 May 1980

Inventor(s) Walter Morozowich

It is certified that error appears in the above-identified patent and that said Letters Patent are hereby corrected as shown below:

Column 2, lines 5-10, that portion of the formula reading:

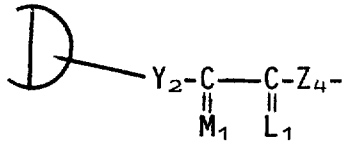 should read 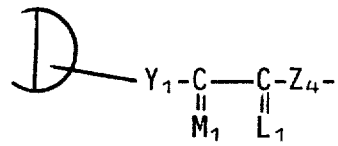

Column 2, line 44, -- (3) $-CH_2CH_2-$ -- should appear;

Column 6, line 15, "claim 49" should read -- claim 40 --.

Signed and Sealed this

Seventeenth Day of February 1981

[SEAL]

*Attest:*

*Attesting Officer*

RENE D. TEGTMEYER

*Acting Commissioner of Patents and Trademarks*